(12) United States Patent
Georgilis et al.

(10) Patent No.: US 10,433,857 B2
(45) Date of Patent: Oct. 8, 2019

(54) BALLOON DILATION CATHETER

(71) Applicant: Bryan Medical, Inc., Cincinnati, OH (US)

(72) Inventors: Andrew J. Georgilis, Cincinnati, OH (US); Michael John Rutter, Cincinnati, OH (US)

(73) Assignee: Bryan Medical, Inc., Cincinnati, OH (US)

( * ) Notice: Subject to any disclaimer, the term of this patent is extended or adjusted under 35 U.S.C. 154(b) by 24 days.

(21) Appl. No.: 15/192,144

(22) Filed: Jun. 24, 2016

(65) Prior Publication Data

US 2017/0367718 A1     Dec. 28, 2017

(51) Int. Cl.
| | | |
|---|---|---|
| *A61B 17/22* | (2006.01) | |
| *A61F 2/958* | (2013.01) | |
| *A61M 25/10* | (2013.01) | |
| *A61M 29/02* | (2006.01) | |

(52) U.S. Cl.
CPC .............. *A61B 17/22* (2013.01); *A61F 2/958* (2013.01); *A61M 25/10* (2013.01); *A61M 29/02* (2013.01); *A61B 2017/22051* (2013.01); *A61F 2230/0078* (2013.01); *A61M 25/104* (2013.01); *A61M 2210/105* (2013.01); *A61M 2210/1025* (2013.01)

(58) Field of Classification Search
CPC .......................... A61M 25/10; A61M 25/1002
See application file for complete search history.

(56) References Cited

U.S. PATENT DOCUMENTS

| | | | | |
|---|---|---|---|---|
| 5,092,873 | A * | 3/1992 | Simpson ........ | A61B 17/320783 604/101.01 |
| 5,352,199 | A * | 10/1994 | Tower ............... | A61M 25/1002 604/103.07 |
| 5,490,839 | A * | 2/1996 | Wang ................ | A61M 25/0045 604/103 |
| 5,645,560 | A * | 7/1997 | Crocker ........... | A61M 25/1002 606/108 |
| 5,669,924 | A * | 9/1997 | Shaknovich ............... | A61F 2/07 604/101.04 |
| 6,120,523 | A * | 9/2000 | Crocker .................... | A61F 2/86 128/898 |
| 6,200,325 | B1 * | 3/2001 | Durcan .................. | A61F 2/958 604/101.05 |
| 6,488,653 | B1 * | 12/2002 | Lombardo ........ | A61M 25/1002 604/101.01 |
| 6,960,186 | B1 * | 11/2005 | Fukaya ............. | A61M 25/1027 604/102.02 |
| 7,771,446 | B2 | 8/2010 | Rutter | |

(Continued)

*Primary Examiner* — Alexander J Orkin
(74) *Attorney, Agent, or Firm* — Taft Stettinius & Hollister LLP; Derek B. Lavender

(57) ABSTRACT

An apparatus for performing a balloon dilation procedure at the site of a stenosis or for deploying a stent in a patient, the apparatus including a single lumen catheter having a proximal end and a distal end, and a high pressure balloon attached to the distal end of the catheter. The high pressure balloon is fabricated from a semi-compliant material that has an average rated burst pressure of between about 15 and about 27 atmospheres of pressure and exhibits a dumbbell-shaped outer periphery when inflated to a first atmospheric pressure and a substantially linear outer periphery when inflated to a second atmospheric pressure.

11 Claims, 5 Drawing Sheets

(56) References Cited

U.S. PATENT DOCUMENTS

| | | | | |
|---|---|---|---|---|
| 2002/0120320 A1* | 8/2002 | Wang | A61F 2/958 | 623/1.11 |
| 2004/0073250 A1* | 4/2004 | Pederson, Jr. | A61F 2/958 | 606/192 |
| 2006/0210605 A1* | 9/2006 | Chang | A61B 17/24 | 424/434 |
| 2007/0066962 A1* | 3/2007 | Rutter | A61M 25/104 | 604/509 |
| 2011/0144742 A1* | 6/2011 | Madrid | A61F 2/2433 | 623/2.11 |
| 2014/0277065 A1* | 9/2014 | Campbell | A61M 25/10184 | 606/192 |
| 2014/0277071 A1* | 9/2014 | Wu | A61M 29/02 | 606/196 |
| 2014/0343348 A1* | 11/2014 | Kaplan | A61B 17/3478 | 600/8 |
| 2015/0217093 A1* | 8/2015 | Tsutsui | A61M 25/1002 | 606/194 |

* cited by examiner

BALLOON DILATION CATHETER

TECHNICAL FIELD

The present invention relates to medical care equipment and procedures for relieving a stenosis or deploying a stent into a patient. In particular, the invention relates to a balloon catheter device for performing dilation of strictures of the patient's airway, including the larynx, trachea or bronchi, vascular system, esophagus, or other areas of the body needing such treatment.

BACKGROUND OF THE DISCLOSURE

The statements in this section merely provide background information related to the present disclosure and should not be construed as constituting prior art.

Management of stenosis of the trachea and bronchi, including laryngotracheal and subglottic stenosis, is one of the most challenging problems for the head and neck surgeon. Subglottic stenosis is a congenital or acquired narrowing of the subglottic airway. In the early twentieth century subglottic stenosis was rare, and most cases occurred in adults. In the 1960's the incidence of acquired subglottic stenosis began to dramatically increase in the neonatal population, most likely the result of increased survival of low-birth-weight infants and the increased use of intubation in this population. In addition, long term intubation has become an accepted alternative to tracheotomy, leading to more and more incidences of tracheal stenosis. Accordingly, the management of this condition has undergone a revolution, and reconstructive surgery efforts have been directed towards this population.

Most patients with stenosis of the airway are referred to and are treated at large academic centers by physicians specially trained in this area. There is a wide range of presentation of subglottic stenosis with similarities and differences in the pediatric age group compared to adults. If the stenosis is severe and congenital, the patient will show signs of airway distress at birth. More commonly, the pediatric patient with subglottic stenosis is a neonate in the intensive care unit who has failed extubation, usually multiple times. Occasionally patients will present in clinic with a tracheotomy and the report of some airway obstruction. Infants with mild subglottic stenosis may present with recurrent croup-like illnesses and poor feeding. Adults usually have a history of prior intubation with symptoms of progressive shortness of breath and noisy breathing.

Airway balloon dilation has been shown to be a safe and effective palliative procedure for treatment of mild congenital and acquired stenosis of the trachea and bronchi. Dilation of luminal human anatomy to treat stenoses can be dated back to the 16th Century with esophageal "bougie" dilation. Specific medical applications of luminal balloon dilation range from alimentary canal and airway dilation to dilation of the vasculature. Airway dilation dates back over 100 years ago with the invention and subsequent use of the first beveled rigid bronchoscopes for stricture management. The use of balloons to dilate airway strictures emerged in the mid-1980's with reports describing more specific utility of this procedure exclusively and in combination with other treatment modalities for airway stenosis. It was not until the early 1990's that the first balloon dilation involving flexible bronchoscopy was described.

Airway balloon dilation can be used to quickly re-establish tracheal or bronchial luminal patency to restore airflow in a way that doesn't cause excessive trauma to the patient. According to Poiseuille's Law, an increase in a tube's radius (such as the trachea or bronchus) can increase airflow by a power of 4 (airflow=radius of the tube$^4$). That is, very small increases in the luminal diameter of the airway can lead to large increases in airflow through the lungs. Literature has reported the use of balloon dilation for the treatment of benign strictures of the airway. Fibrotic strictures, such as those secondary to tuberculosis, long-term endotracheal or tracheostomy tube placement, berylliosis, Wegener's granulomatosis, or sarcoidosis have been shown to be treatable with airway balloon dilation therapy with general success. Additionally, balloon dilation has been useful in treating strictures secondary to major surgical interventions such as lung transplantation, sleeve resection, bronchial re-implantation, and lobectomy. For the purpose of treating strictures secondary to malignant obstruction, dilation therapy can be used alone or in combination with other techniques such as surgical resection, cryotherapy, laser therapy, and stent placement, depending on the desired outcome for the patient.

Treatment with airway dilation can involve the clinician inserting increasingly larger tubes into the airway (e.g. endotracheal tubes or cat-tail (bougie) dilators), which creates significant shear forces on the airway mucosa. Although safe when performed by a skilled clinician, such a procedure sometimes induces unwanted trauma to the airway in the form of deep lacerations and hemoptysis. Further, current dilation practices do not permit dilation of a tracheal stenosis that is distal to a narrowing of the proximal airway (i.e. a mild subglottic stenosis).

Current airway balloon dilation procedures are typically carried out using angioplasty balloons; however, several limitations to the use of angioplasty balloons become evident when used on the airway. For example, it may be difficult to adequately ventilate the patient during the dilation period, since the typical angioplasty balloon does not include a connection to an oxygen source. Further, the shape of the angioplasty balloon may predispose the balloon to slide out of place during dilation, or the balloon may be limited to the amount of pressure that can be applied before the balloon bursts. Also, the typical angioplasty balloon can usually stretch the airway lumen but not permanently dilate it. Other factors associated with failure of airway balloon dilation include previous attempts at endoscopic repair, circumferential scarring, and loss of cartilaginous support.

U.S. Pat. No. 7,771,446, the disclosure of which is incorporated in its entirety herein by this reference, provides a balloon dilator for the airway of a patient that is able to allow ventilation of the patient during balloon inflation, as well as provides increased inflation pressures during balloon dilation of the airway. In particular, the balloon dilator is capable of deploying a stent in a patient at the site of a stenosis by utilizing an inflatable outer dumbbell-shaped balloon that will not slip out of place in the patient's airway or other body lumen during balloon inflation. By utilizing a dumbbell shape, the balloon is prevented from slippage by inflating at either end (i.e. on either side of the stenosis) before the central section inflates, thereby allowing the central section of the outer balloon to stay in position over the stenosis during inflation. To accomplish this during the inflation process, the proximal and distal ends of the outer balloon inflate first, thereby forming the "dumbbell" shape, and as a result, trapping the stenotic airway segment at the central portion of the balloon. Then, as the pressure in the balloon is increased, the central portion of the balloon fully inflates at the site of the stenosis.

In addition to the outer balloon, the dilator of U.S. Pat. No. 7,771,446 also includes one or more inner balloons that allow higher dilation pressures to be generated from inside the outer balloon. In accordance with certain embodiments, the inner balloons are contained inside the outer balloon and are simultaneously inflatable within the outer balloon. In accordance with other embodiments, at least one inner balloon inside the outer balloon is capable of inflating separately from the outer balloon.

While the dilator of U.S. Pat. No. 7,771,446 is very effective, it would be advantageous to provide an airway balloon dilator that does not slip out of place and provides increased inflation pressures during balloon dilation without utilizing a plurality of balloons to achieve such advantages. The present invention is intended to address these deficiencies within the prior art.

SUMMARY OF THE DISCLOSURE

In accordance with one aspect of the present application, an apparatus for performing a balloon dilation procedure at the site of a stenosis or for deploying a stent in a patient is provided. According to this embodiment, the apparatus includes a single lumen catheter having a proximal end and a distal end and a high pressure balloon attached to the distal end of the catheter. The high pressure balloon is fabricated from a semi-compliant material having an average rated burst pressure of between about 15 and about 27 atmospheres of pressure and exhibiting a dumbbell-shaped outer periphery when inflated to a first atmospheric pressure and a substantially linear outer periphery when inflated to a second atmospheric pressure.

Still other objects and benefits of the application will become apparent from the following written description along with the accompanying figures.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein.

Figure 1:
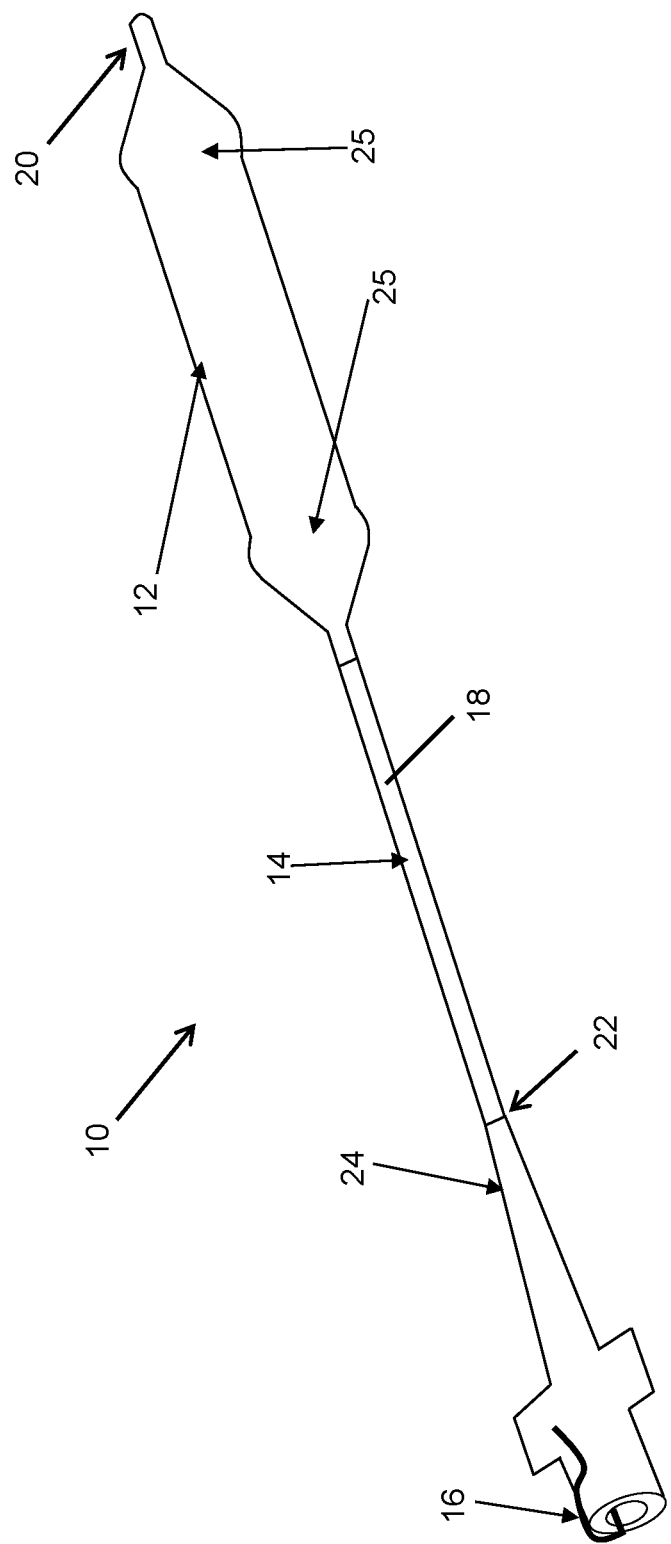
FIG. 1 represents a perspective view of an illustrative balloon dilation catheter device in accordance with one aspect of the present invention.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

The present invention provides an apparatus for performing a balloon dilation catheter procedure at the site of a stenosis or for deploying a stent in a patient. In particular, the balloon dilation catheter procedure can be used for treating any stenosis or area in need of a stent in a patient, as well as for performing dilation of a lumen in a patient's larynx, trachea or bronchi, vascular system, esophagus, or other areas of the body.

As will be described in greater detail below, the balloon dilation catheter includes a single lumen catheter with an inflatable high pressure balloon near the distal tip. In accordance with certain aspects herein, the balloon dilation catheter is insertable into a patient to a desired location with the assistance of a stylet. Once the balloon is inserted to the desired location within the patient, the stylet can then be removed and the high pressure balloon inflated from its deflated configuration. In accordance with certain embodiments, a luer lock at the proximal end of the catheter shaft is used for placement of the stylet and for injecting sterile water into the balloon. In addition, radiopaque markers can also be located on the catheter inside the balloon to confirm the balloon placement under fluoroscopy.

One aspect of the invention provides an apparatus for performing an airway balloon dilation procedure at the site of a stenosis in the airway of a patient. In accordance with certain aspects, the apparatus comprises a balloon that when deflated has a narrow diameter, but inflates in a dumbbell shaped fashion (i.e., the outer periphery of the balloon exhibits a dumbbell shaped configuration) whereby the proximal and distal aspects of the balloon inflate before the central aspect of the balloon. This can be achieved by utilizing a semi-compliant balloon that exhibits shape memory properties, as well as by providing the central half of the balloon with a greater wall thickness than the proximal and distal portions of the balloon. The advantage of this configuration is that once the balloon is inflated across a stenosis, the proximal and distal portions of the balloon inflate prior to the central section. Because the proximal and distal portions inflate first, the balloon develops hubs at those respective regions, which in turn, encourages the balloon to be held in place proximate the stenosis and thereby prevented from slipping during the remainder of the inflation process. As pressure inside the balloon increases, the central aspect of the balloon eventually inflates, thereby expanding the stenosis. When the balloon is fully inflated, the outer periphery of the balloon develops a substantially linear shape exhibiting a uniform diameter from its proximal end to its distal end.

It should be noted that while the present balloon dilation catheter is particularly useful as an airway dilator, in accordance with certain aspects herein, the device can also be used to place and deploy an expandable stent within a targeted anatomical region of a patient. According to these aspects, a stent is placed over the central aspect of the balloon, and once the proximal and distal portions of the balloon are inflated, the stent is then locked into position over the central aspect of the balloon.

Referring now to FIG. 1, a balloon dilation catheter 10 in accordance with one embodiment of the present invention is shown. In accordance with this embodiment, the apparatus comprises a single chamber high pressure balloon 12 that is attached to a single lumen catheter 14 at its distal tip. A stylet 16 is provided to facilitate advancement of the balloon dilation catheter 10 to a desired location within a patient. In accordance with certain aspects herein, the stylet 16 is removed before inflation of the high pressure balloon 12. A central lumen 18 extends longitudinally throughout the catheter 14 and has a distal end 20 fixedly attached to the distal end of the balloon 12, while the proximal end 22 of the central lumen 18 terminates into a luer lock 24, which is in turn used to place the stylet 16 and for injecting sterile water into the balloon 12. The central lumen 18 of the catheter 14 serves as the inflation lumen for the balloon 12, and as such, is configured to be filled with saline or water to thereby achieve a desired level of atmospheric inflation pressure within the balloon. It should be understood and appreciated that the amount of atmospheric pressure placed into the balloon will be influenced by and depend upon the size of the balloon being utilized. For instance, in accordance with certain aspects herein when the balloon size is between about 5 and about 10 mm, the atmospheric pressure is generally between about 14 and about 19 atmospheres (atm) of pressure, and more particularly about 17 atmospheres (atm) of pressure. In accordance with certain illustrative embodiments in which the balloon size is between about 12 and about 16 mm, the atmospheric pressure is generally between about 8 and about 12 atmospheres (atm) of pressure, and more particularly about 10 atmospheres (atm) of pressure.

The stylet 16 is slidably positioned through the catheter 14 during a dilation procedure to advance the catheter within an airway or targeted anatomical passageway (e.g., at a stenosis site). The balloon 12 may then be actuated to an expanded state to open or dilate the targeted anatomical passageway and then deflated back to a collapsed state once the dilation procedure is completed. To assist with placing the balloon 12 at the desired location within the airway or targeted anatomical passageway of a patient during a dilation procedure, the balloon dilation catheter 10, in accordance with certain embodiments, may include some form of indicia 25 if desired. More particularly, to enable the medical technician to orient a given section of the balloon proximate the stenosis site or other such stricture, the balloon dilation catheter can include one or more indicia 25 that are viewable under either fluoroscopy or via direct visualization procedures, such as through an endoscope. It should be understood and appreciated herein that the indicia 25 can be placed on the catheter 14 relative to one or more sections of the balloon and can be made of a radiopaque material to assist the technician in positioning the balloon 12 under a fluoroscope. Radiopaque materials are known within the art and may include, but are not necessarily limited to, gold, platinum, or tantalum. It should be understood that other types of radiopaque materials can also be applied to or deposited on the surface of the catheter 14, and can include, for instance, ink, paint, or polymer containing barium or tantalum, etc.

It should be understood and appreciated herein that the balloon catheter 14 may have any number of suitable sizes, shapes and configurations. In addition, the balloon 12 may also have different lengths and diameters to accommodate different patient anatomies. Accordingly, it should be understood that the various dimensions and configurations provided herein are only intended to be illustrative in nature and should not be perceived as limiting the teachings of the present invention. To this end, those of skill in the art will appreciate and understand that different sized catheters and/or balloons may be necessary for given procedures, as well as to accommodate the different anatomical sizes of the patients undergoing the procedure. By way of illustration, however, in accordance with certain aspects herein, the overall length of the balloon catheter 14 (i.e., from the proximal end 22 to the distal end 20 of the catheter shaft 14) may be around 53 cm (or around 55 cm when also including the length of the luer lock together with the catheter shaft).

As used herein, the term "working length" is intended to refer to the portion of the balloon 12 that exhibits a linear (i.e., non-hubbed) shape when inflated to an atmosphere pressure between about 1 and 6 atmospheres (atm). In other words, this linear portion of the balloon refers to the central area or portion 38 of the balloon that is between the proximal and distal end (hubbed) portions 34, 36 of the balloon that interfaces and dilates the stricture upon full inflation. It should be understood and appreciated herein that the working length of the balloon 12 will be influenced by and depend upon the size of the balloon being utilized. For instance, in accordance with certain aspects herein when the balloon size is between about 5 and about 10 mm, the working length of the balloon 12 may be about 30 mm. In accordance with certain illustrative embodiments in which the balloon size is between about 12 and about 16 mm, the working length of the balloon 12 may be about 40 mm. Once again, it should be understood and appreciated herein that a combination of balloon diameters and lengths may be provided as needed so that a physician may choose an appropriate size for an adult or pediatric patient. As such, the present invention is not intended to be limited herein. Table 1 illustrates various non-limiting balloon dilation catheter and balloon sizes and corresponding characteristics in accordance with certain aspects of the present invention.

TABLE 1

| Balloon Dilation Catheter Size | Balloon size (mm) | Balloon Working Length (mm) | Illustrative Use Pressure (ATM) | Catheter OD (mm) | Catheter Length (cm) (including luer lock) |
|---|---|---|---|---|---|
| 5 × 30 mm | 5 | 30 | 17 | 1.55 | 55 |
| 6 × 30 mm | 6 | 30 | 17 | 1.55 | 55 |
| 7 × 30 mm | 7 | 30 | 17 | 1.55 | 55 |
| 8 × 30 mm | 8 | 30 | 17 | 1.55 | 55 |
| 9 × 30 mm | 9 | 30 | 17 | 1.55 | 55 |
| 10 × 30 mm | 10 | 30 | 17 | 2.34 | 55 |
| 12 × 40 mm | 12 | 40 | 10 | 2.34 | 55 |
| 14 × 40 mm | 14 | 40 | 10 | 2.34 | 55 |
| 16 × 40 mm | 16 | 40 | 10 | 2.34 | 55 |
| 18 × 40 mm | 16 | 40 | 10 | 2.34 | 55 |

Prior to use, the balloon dilation catheter 10 is provided in sterile packaging and with a protective sheath covering the balloon 12. After removing the catheter 14 from the packaging and protective sheath, it is wiped down with a gauze pad soaked in sterile water. The catheter 14 is then gently advanced into the airway of a patient and to the site of the stricture under endoscopic visualization. The balloon 12 portion of the device 10 is then centered across the restriction and the stylet 16 is removed while holding the catheter 14 securely in place. The balloon dilation catheter luer 24 is attached to the inflation device (not shown) and the balloon 12 is inflated to a desired pressure with sterile water. In accordance with certain aspects herein, the balloon 12 is monitored during the inflation process via endoscopy to assess the diameter, shape, and position of the balloon so that it can be ensured that the proximal end 22 of the balloon remains proximate to the stricture.

After the dilation process is completed, and while the endoscopic view of the balloon 12 is maintained, the balloon is then completely deflated using a vacuum. Before the balloon 12 is removed from the airway, a visual confirmation can be made to verify that the balloon 12 is fully deflated. If additional inflations are required, the balloon 12 can be gently re-wrapped and compressed starting at the distal end as a vacuum is applied.

As should be understood and appreciated herein, medical balloons are generally referred to as compliant, non-compliant and semi-compliant. As is known generally within the art, balloon compliance is a term used to describe the change in a balloon's diameter as a function of pressure. Low pressure compliant medical balloons are typically formed from elastomers such as latex, polyurethane and other thermoplastic elastomers and may expand by 100% or greater upon inflation. Compliant medical balloons are typically used for fixation and occlusion.

High pressure non-compliant dilation balloons, on the other hand, expand very little, if at all, when pressurized from a nominal diameter to a rated burst pressure. As is generally known, the rated burst pressure of a medical balloon refers to the maximum pressure at which there is a statistical 95% confidence level that 99.9% of the population of balloons will not burst. Typically, high pressure non-compliant balloons may have rated burst pressures of up to 20 atmospheres or higher and are formed from relatively inelastic materials, such as polyethylene terephthalate (PET) films, which provide high tensile strength and may be used to form balloons with thin walls having high burst pressures.

Semi-compliant medical balloons, by contrast, exhibit a moderate degree of expansion when pressurized from an operating pressure (e.g., the pressure at which the balloon reaches its nominal diameter) to its rated burst pressure. As compared to non-compliant balloons, semi-compliant balloons are less stiff and provide better puncture resistance qualities. However, the tensile strength of semi-compliant medical dilation balloons is typically less than that of non-compliant balloons. As a result, dilation balloons formed from semi-elastic materials typically must be fabricated with thicker walls in order to achieve the same burst pressures as the non-compliant balloons. By having a thicker wall, the diameter of the balloon catheter assembly and the size of the introducer used to introduce the semi-compliant balloon as part of the dilation procedure must also be increased.

In accordance with certain aspects herein, the high pressure balloon 12 is formed from a semi-compliant material and has a rated burst pressure of up to about 27 atmospheres (atm). As those of skill in the art will understand and appreciate herein, the larger the balloon diameter, the lower the burst pressure. For illustrative purposes, Table 2 shows exemplary test data of various rated burst pressures of balloons as a function of balloon size and diameter and at recommended use pressures in accordance with the present teachings. The standard deviation of the rated burst pressures, in accordance with these illustrative examples, is a measure of the consistency of the burst pressure over about 40 different tests.

TABLE 2

| Balloon Size (mm) | Avg. Burst Pressure (ATM) | Std. Dev. (ATM) | Avg. diameter at recommended use pressure (mm) |
| --- | --- | --- | --- |
| 5 × 30 | 23.06 | .85 | 5.06 |
| 7 × 30 | 23.05 | 1.26 | 6.91 |
| 8 × 30 | 26.09 | .94 | 7.82 |
| 9 × 30 | 24.85 | 1.3 | 8.97 |
| 10 × 30 | 24.96 | .72 | 9.75 |
| 12 × 40 | 16.84 | .59 | 11.83 |
| 14 × 40 | 16.37 | .73 | 13.86 |
| 16 × 40 | 15.42 | .78 | 16.23 |

It should be understood and appreciated herein that the present invention provides a balloon that is safer and has improved treatment efficacy as compared to other conventional medical dilation balloons within the industry. More particularly, unlike conventional balloons, the balloon of the present invention has a recommended inflation pressure and rated/tested burst pressure that is not only unique, but also inflates (i.e., has an expansion curve ratio) that is much more consistent than compliant balloon structures. For instance, there is a difference of approximately 7.4 atmospheres (atm) of pressure between the recommended inflation setting for balloons sized 5 mm, 6 mm, 7 mm, 8 mm, 9 mm and 10 mm and a difference of 6.2 atm between the recommended inflation pressure and the rated burst pressure for balloons sized 12 mm, 14 mm, 16 mm and 18 mm. This difference in suggested inflation pressure versus the burst pressure is significant and unique as compared to other conventional balloons within the medical dilation industry.

Before describing the illustrative balloons 12 of the present invention in more detail, it should be noted that, as used herein, when the pressure of fluid inside the balloon 12 is reduced, this process may be referred to as "deflating," even if the material forming the balloon 12 does not elastically shrink, since the balloon 12 may nevertheless flexibly collapse in response to reduced fluid pressure. Thus, it should be understood that the use of terms such as "inflate," "inflated," "deflate," and "deflated" does not necessarily mean that the material forming the balloon 12 undergoes any elastic stretching or shrinking as the fluid pressure within the balloon 12 changes.

Figure 2:
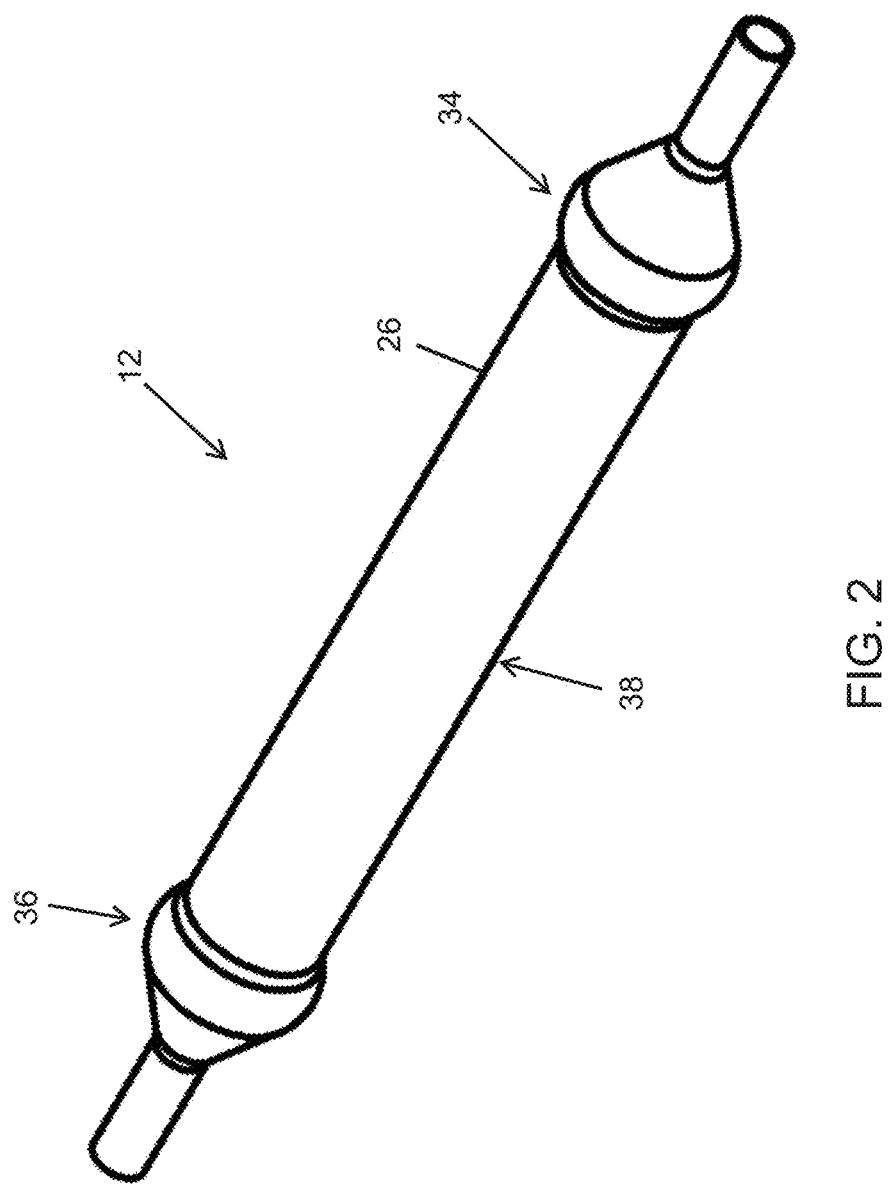
FIG. 2 represents a perspective view of an illustrative high pressure balloon that has been inflated to approximately 2 ATM in accordance with one illustrative aspect of the present invention.
Figure 3:
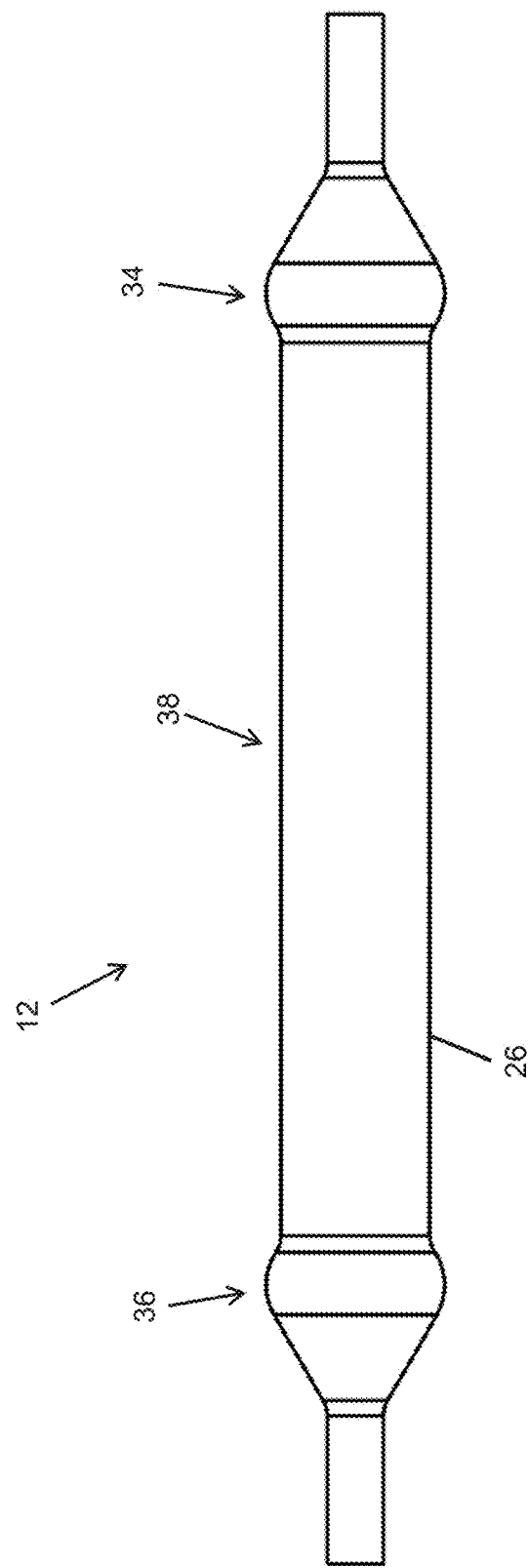
FIG. 3 represents a side view of the illustrative high pressure balloon of FIG. 2.

With reference now to FIGS. 2-3, an illustrative high pressure balloon 12 is illustrated at less than 2 ATM of inflation. In accordance with this embodiment, the balloon 12 has an external surface 26 that is dumbbell or dog bone shaped. More particularly, and as will be explained in greater detail below, the balloon 12 is configured to have a segmented dumbbell shape during the inflation process, such that, prior to reaching maximum inflation, the proximal 34 and distal 36 portions of the balloon have a larger diameter than the central section 38 of the balloon. As those of skill in the art will understand and appreciate herein, to achieve this shape, a semi-complaint shape memory polymer can be used that is capable of allowing the proximal 34 and distal 36 ends of the balloon to inflate before the central portion 38 of the balloon inflates. As used herein, a "shape memory polymer" refers to a polymeric material whose qualities have been altered to give them dynamic shape memory properties. As is generally known within the art, polymers possessing shape memory properties, through the use of stimuli, can exhibit radical changes between rigid and elastic polymeric states. Moreover, the stored mechanical energy attained during the reconfiguration of these materials allows the memory or recovery qualities of these polymers to be exhibited. In accordance with certain aspects herein, the shape memory polymer that is used to form the balloon 12 is a nylon material.

To achieve the hub-like and dumbbell shaped outer periphery that is unique to the present invention, in accordance with certain aspects herein, a semi-compliant polyamide (nylon) balloon is blow molded in such a manner that the hub-like portions of the balloon are memory shaped into the structure. More particularly, as should be appreciated herein, the properties associated with the polyamide (nylon) material exhibit a specific expansion limitation feature, such that during the blow molding process, the proximal 34 and distal 36 portions of the balloon can be stretched to their maximum expansion limits, while leaving the central section 38 not expanded to such a degree. As a result of maximally expanding the proximal 34 and distal 36 portions of the balloon during the blow molding process, the balloon is able to develop a hub-like feature that is memory shaped into the balloon structure. Accordingly, when the balloon 12 is deployed within a patient as part of a dilation process, the proximal 34 and distal 36 portions recover, when begin inflated, to their memory shaped expansion limitation features before the central section, thereby creating a dumbbell-shaped outer periphery that is defined by the two hub-like features at the respective locations of the proximal 34 and distal 36 regions. As the atmospheric pressure increases, the outer diameter of the central section 38 eventually matches the outer diameter of the hub-like portions, thereby creating an outer periphery for the balloon 12 that is substantially linear in shape (i.e., exhibits a uniform outer diameter across the entire balloon).

Figure 4:
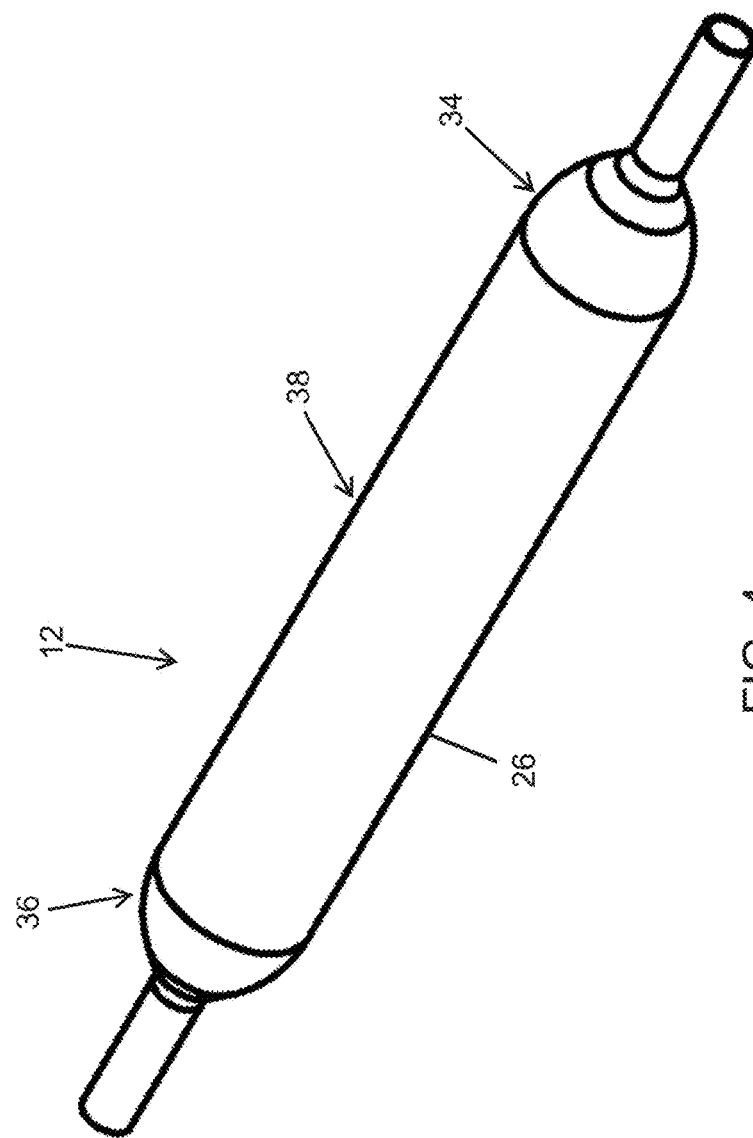
FIG. 4 represents a perspective view of the illustrative high pressure balloon of FIG. 2 inflated to approximately 17 ATM in accordance with one illustrative aspect of the present invention.
Figure 5:
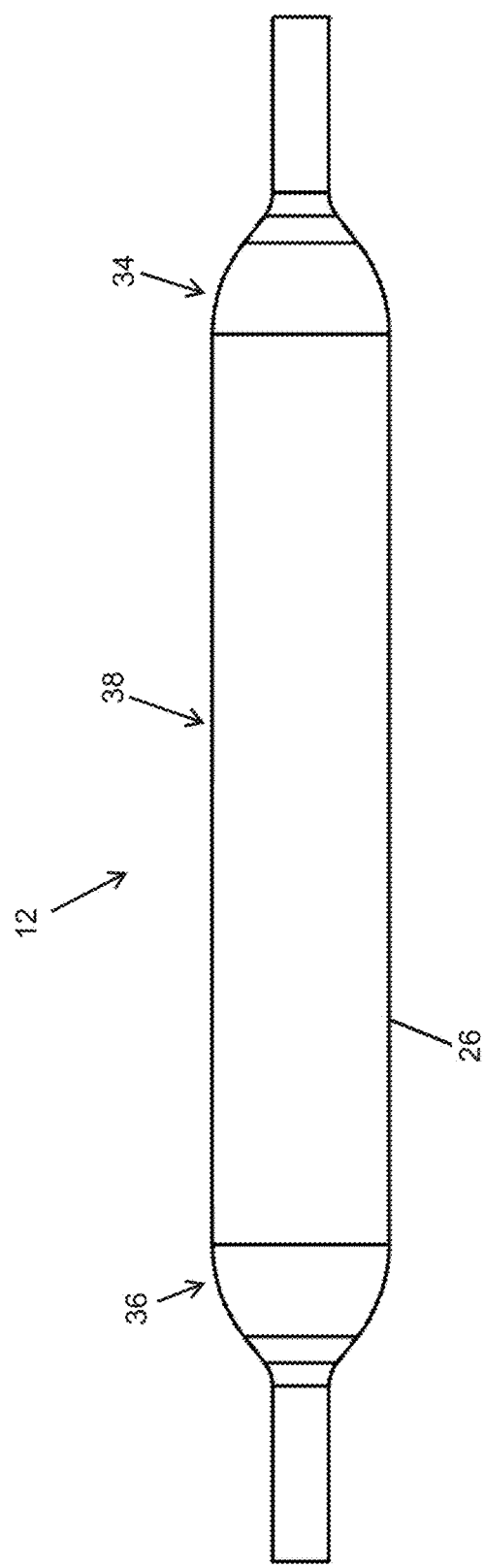
FIG. 5 represents a side view of the illustrative high pressure balloon of FIG. 4.

In addition to exhibiting shape memory properties, the balloon 12 may also be formed such that the proximal 34 and distal 36 ends have a decreased balloon wall thickness as compared to the central section 38 of the balloon, which may have an increased balloon wall thickness. It should be understood and appreciated herein that the wall thickness of the balloon 12 will be influenced by and depend upon the size of the balloon being utilized. For instance, in accordance with certain aspects in which the balloon size is 8 mm, the wall thickness at the central section 38 is about 0.0020 inches and the wall thickness at the proximal 34 and distal 36 ends is about 0.0017 inches. By contrast, in accordance with certain illustrative embodiments in which the balloon size is 10 mm, the wall thickness at the central section 38 is between about 0.0022 inches and about 0.0023 inches, while the wall thickness at the proximal 34 and distal 36 ends is between about 0.0019 inches and about 0.0020 inches. As a result of these properties, during inflation, the outer periphery of the balloon achieves a dumbbell shaped configuration in which the proximal 34 and distal 36 ends, which are positioned on opposite sides of the stenosis, inflate before the central section 38 inflates. More particularly, as the balloon 12 inflates, the proximal and distal end portions 34, 36 take the shape of dumbbell like hubs that in turn contact the surface of the airway and thereby cause the balloon 12 to be held into place proximate the stenosis site. In other words, during inflation, the proximal 34 and distal 36 ends of the balloon 12 inflate first, forming the "dumbbell" shape, and thereby trapping the stenotic airway segment at the central portion 38 of the balloon 12, so that the balloon 12 does not slip out of position. Then, as the pressure in the balloon is increased, the central portion 38 of the balloon fully inflates at the site of the stenosis. FIGS. 4-5 show a balloon 12 that has been inflated to approximately 17 ATM and in which the central portion 38 has now been fully inflated and exhibits a substantially linear outer periphery.

In practice, the balloon dilation procedure is typically performed at the site of a stenosis in the airway of a patient (i.e. the larynx, trachea or bronchi). Using the apparatus shown in FIG. 1, the surgeon or clinician inserts the balloon dilation catheter 10 into the airway until the balloon 12 is positioned across the stenosis. At this point, the surgeon or clinician inflates the balloon 12 to cause and allow the external surface 26 of the balloon 12 to expand upon and dilate the stenosis. Under direct visualization, the balloon is typically inflated for about 30 to about 120 seconds. It should be understood and appreciated herein that repeat inflation-deflation cycles can be performed if airway narrowing remains after the initial dilation attempt.

During a balloon dilation procedure, the size of the balloon is first selected by the clinician, which depends upon the size of the stenosis in the patient's airway. As is explained above in accordance with certain aspects herein, the balloon size may be between about 30 mm and about 40 mm in length. Once the balloon is chosen, the balloon 12 is positioned over the stenosis and then dilated to the desired pressure with a balloon pump, typically to between about 14 and about 19 atmospheres (atm) for balloons sized between about 5 and about 10 mm, and between about 8 and about 12 atmospheres (atm) for balloons sized between about 12 and about 16 mm.

After these pressures are maintained for a predetermined period of time, typically between about 30 to about 120 seconds, the balloon is deflated and the clinician determines if repeat inflation is necessary. Repeat inflation can be safely performed if there is no obvious trauma to the airway.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. An apparatus for performing a balloon dilation procedure at the site of a stenosis within the airway of a patient, comprising:
   a single lumen catheter having a proximal end and a distal end; and
   a high pressure balloon attached to the distal end of the catheter, the balloon being fabricated from a semi-compliant material having an average rated burst pressure of between about 15 and about 27 atmospheres of pressure and a use inflation pressure, the balloon having a central portion positioned between proximal and distal hubbed ends;
   wherein, the central portion of the balloon maintains a substantially linear profile when the balloon is inflated to an atmospheric pressure between about 1 and 6 atmospheres;
   wherein, the high pressure balloon exhibits a dumbbell-shaped outer periphery when inflated to a first atmospheric pressure and a substantially linear outer periphery when inflated to a second atmospheric pressure;
   wherein, the first atmospheric pressure is less than the second atmospheric pressure; and
   wherein, the use inflation pressure is between about 6 and about 8 atmospheres less than the average rated burst pressure.

2. The apparatus of claim 1, further comprising radiopaque markers on the single lumen catheter.

3. The apparatus of claim 1, further wherein, the central portion has a first wall thickness of about 0.0020 inches and the distal and proximal ends each have a second wall thickness of about 0.0017 inches.

4. The apparatus of claim 1, wherein the balloon has a diameter of between about 5 millimeters and about 10 millimeters when filled with a fluid to an atmospheric pressure of between about 14 and 19.

5. The apparatus of claim 1, wherein the balloon has a diameter of between about 5 millimeters and about 10 millimeters when filled with a fluid to an atmospheric pressure of about 17.

6. The apparatus of claim 1, wherein the balloon has a diameter of between about 12 millimeters and about 16 millimeters when filled with a fluid to an atmospheric pressure of between about 8 and about 12.

7. The apparatus of claim 1, wherein the balloon has a diameter of between about 12 millimeters and about 16 millimeters when filled with a fluid to an atmospheric pressure of about 10.

8. The apparatus of claim 1, wherein the balloon has indicia thereon that is viewable with an endoscope or a fluoroscope.

9. The apparatus of claim 1, wherein the catheter has a length of from about 53 cm to about 55 cm.

10. The apparatus of claim 1, wherein the balloon has a diameter of between about 5 millimeters and about 10 millimeters and a working length of about 30 millimeters.

11. The apparatus of claim 1, wherein the balloon has a diameter of between about 12 millimeters and about 16 millimeters and a working length of about 40 millimeters.

* * * * *